US00PP32977P2

(12) United States Plant Patent
Kamstra

(10) Patent No.: US PP32,977 P2
(45) Date of Patent: Apr. 13, 2021

(54) POINSETTIA PLANT NAMED 'EURZ0019'

(50) Latin Name: *Euphorbia pulcherrima*
Varietal Denomination: EURZ0019

(71) Applicant: SYNGENTA CROP PROTECTION AG, Basel (CH)

(72) Inventor: Silvan Adelmar Kamstra, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/602,877

(22) Filed: Dec. 16, 2019

(30) Foreign Application Priority Data

Dec. 11, 2019 (QZ) ..... PBR 2019/3377

(51) Int. Cl.
*A01H 5/02* (2018.01)
*A01H 6/38* (2018.01)

(52) U.S. Cl.
USPC ..... Plt./303
CPC ..... *A01H 6/38* (2018.05)

(58) Field of Classification Search
USPC ..... Plt./303
CPC ..... A01H 5/02
See application file for complete search history.

(56) References Cited

PUBLICATIONS

PLUTO UPOVROM Plant Variety Database Citation for 'EURZ0019' as per QZ PBR 20193377; filed Dec. 12, 2019; 1 page.*

* cited by examiner

*Primary Examiner* — Kent L Bell
(74) *Attorney, Agent, or Firm* — Dale Skalla

(57) ABSTRACT

A new Poinsettia plant named 'EURZ0019' particularly distinguished by the distinct red bract color with white spots, dark green foliage, and strong vigor with good branching and strong stems.

1 Drawing Sheet

Latin name of the genus and species of the plant claimed: *Euphorbia pulcherrima.*

Varietal denomination: 'EURZ0019'.

BACKGROUND OF THE NEW PLANT

The present invention comprises a new Poinsettia, botanically known as *Euphorbia pulcherrima*, and hereinafter referred to by the variety name 'EURZ0019'.

'EURZ0019' is a product of a naturally occurring mutation. The new cultivar has red bract color with a variable number of white colored spots on these bracts. These white colored spots appear in the final growing weeks on the bracts and during times these will increase in size and number. The variety has medium size inflorescences with bracts a little upright directed, dark green foliage, and strong vigor with good branching, like the parent variety 'Fismars 339'.

'EURZ0019' originated as a naturally occurring mutation discovered among greenhouse plants of the parent variety 'Fismars 339' (U.S. Plant Pat. No. 21,054) in Enkhuizen, The Netherlands in fall to winter 2016.

A greenhouse crop was developed from the first mutated plant and evaluated for its unique spotted bracts. These plants were multiplied separately and examined during next fall-winter flowering for uniformity and stability of the new combination of characteristics.

BRIEF SUMMARY OF INVENTION

Horticultural examination of plants grown from cuttings of the plant initiated in April 2017, and continuing thereafter, has demonstrated that the combination of characteristics as herein disclosed for 'EURZ0019' are firmly fixed and are retained through successive generations of asexual reproduction.

'EURZ0019' has not been observed under all possible environmental conditions. The phenotype may vary significantly with variations in environment such as temperature, light intensity and day length.

A Plant Breeder's Right for this cultivar was applied for in the European Union on Dec. 11, 2019, No. 2019/3377. 'EURZ0019' has not been made publicly available prior to the effective filing date of this application, notwithstanding any disclosure that may have been made less than one year prior to the effective filing date of this application by the inventor or another who obtained 'EURZ0019' directly from the inventor.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

The accompanying photographic drawing shows typical flower and foliage characteristics of 'EURZ0019' with colors being as true as possible with an illustration of this type. The photographic drawings show flowering potted plants of the new variety.

Figure 1:
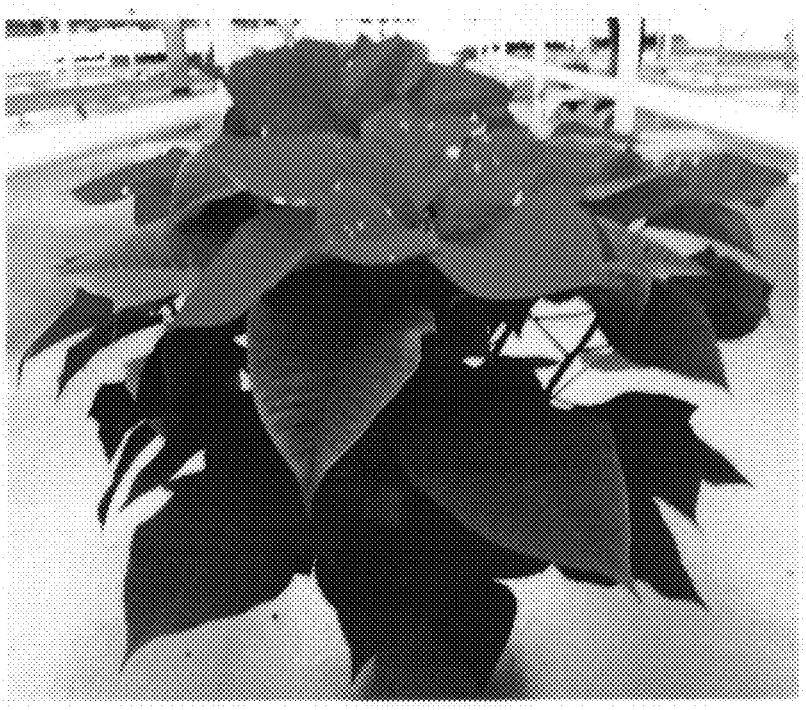

FIG. 1 was taken on Dec. 9, 2019 and shows a view of the bracts from the top of plant, on a plant about 21 weeks old.

Figure 2:
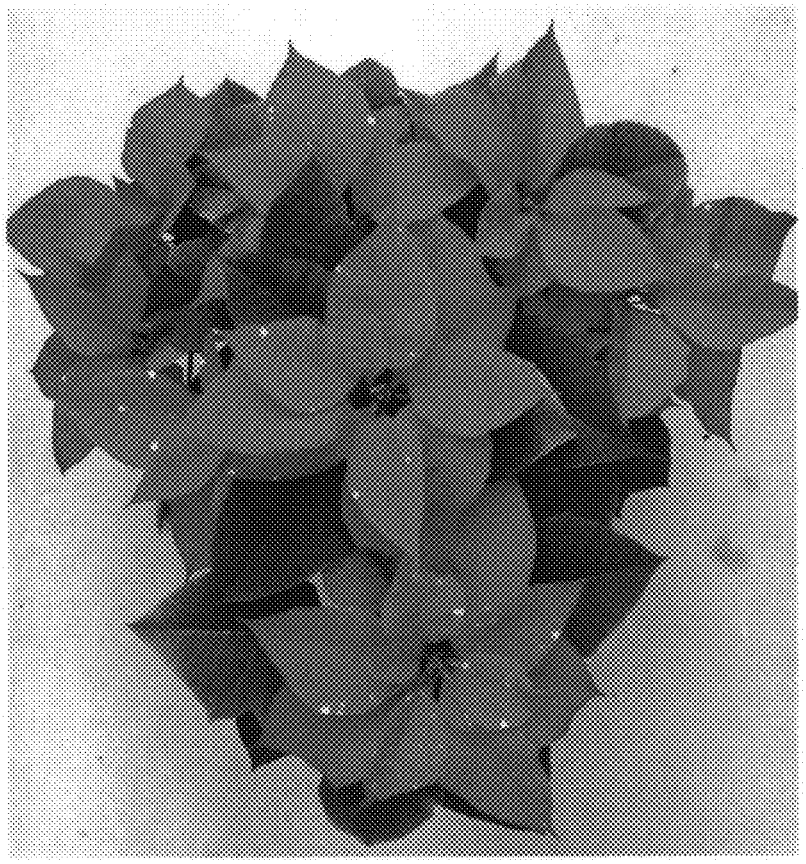

FIG. 2 was taken on Dec. 9, 2019 and shows a side view of the same plant.

DETAILED BOTANICAL DESCRIPTION

The measurements were taken in Enkhuizen, The Netherlands at the end of November 2019 on 21 weeks old plants growing in a greenhouse. Culture of these plants had started in late June 2019 with planting rooted cuttings in 19 cm pots and terminal pinching about 2 weeks later. The plants were grown under natural day light in the fall (no black cloth to initiate earlier flowering) and at the moderately warm temperature of 18° C. for the bench heating. No use of Plant Growth Regulators (PGR).

Color references are made to The Royal Horticultural Society Colour Chart (R.H.S.) 2001.

TABLE 1

DIFFERENCES BETWEEN THE NEW VARIETY 'EURZ0019', THE PARENT 'FISMARS 339' AND A SIMILAR VARIETY

| | 'EURZ0019' | 'Fismars 339' | 'Fismars Pink' (U.S. Plant Pat. No. 18,866) |
|---|---|---|---|
| Bract color: | Red with white spots (RHS 45B + 155A) | Red (RHS 45B) | Pink (RHS 55A) |

Plant:

*Form, growth and habit.*—Shrub, with the branches slanting upright, good branching.

*Plant height (inflorescence included).*—25-30 cm.

*Plant width.*—40-50 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155B but whiter.

Foliage:

*Arrangement.*—Alternate, 6-11 leaves per branch.

*Immature, leaf color, upper surface.*—Approximately RHS 147A.

*Lower surface.*—RHS 137B.

*Mature, leaf color, upper surface.*—RHS 147A.

*Lower surface.*—RHS 137B.

*Length.*—11-12 cm.

*Width.*—7.5-8.5 cm.

*Shape.*—Ovate, with almost no lobes.

*Base shape.*—Truncate to obtuse.

*Apex shape.*—Acuminate.

*Margin.*—Entire; lobes, when present mostly rounded.

*Aspect.*—Leaf blades are horizontally or slightly downwards directed.

*Texture, upper surface.*—Smooth.

*Lower surface.*—Smooth, apart from the protruding veins.

*Color of veins, upper surface.*—RHS 144B and very light RHS 183D for the central vein at the base, turning to RHS 144B towards the leaf tip.

*Color of veins, lower surface.*—RHS 147C, central vein RHS 183D fading towards the leaf tip.

*Venation pattern.*—Pinnate.

*Petiole color, upper surface.*—RHS 187B to RHS 187C.

*Lower surface.*—RHS 184B.

*Length.*—4.5 cm.

*Diameter.*—0.35 cm.

*Aspect.*—Horizontally to slightly upward directed.

*Texture.*—Glabrous.

Stem:

*Quantity of main branches per plant.*—About 4 to 7.

*Color of stem.*—Mix of RHS 183D and RHS 147B.

*Length of stem.*—12-17 cm.

*Diameter.*—0.6-0.8 cm.

*Length of internodes.*—1-2 cm.

*Texture.*—Glabrous.

*Color of peduncle.*—RHS 144B to RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically (opening of the stamen, shedding of pollen).*—Late November.

*Flowering, commercially (sufficiently colored bracts).*—Mid November.

*Flowering response time.*—About 7-7.5 weeks from equinox.

*Duration of flowering.*—Depends on light and environment, at least 4-6 weeks of shelf life.

*Fragrance.*—Absent.

*Shape of inflorescence.*—Rosette-like whorl, star-shaped; bracts borne nearly horizontally to weakly funnel-shaped (slanting upright); tight center.

*Diameter of inflorescence.*—30 cm.

*Inflorescence, vertical diameter.*—5-8 cm.

*Number of completely colored bracts per inflorescence (sized over 2 cm).*—5-7.

*Single bract, shape.*—Ovate with relatively long, pointed tips, without or with weak lobes.

*Bract margin descriptor.*—Between undulate and entire.

*Bract, apex.*—Acuminate.

*Bract, base.*—Weakly rounded.

*Single bract, length of blade.*—Up to 13.5 cm, younger bracts diminishing in size.

*Single bract, width of blade.*—7.5-11.5 cm.

*Bract color, upper side.*—RHS 45B+SPOTS OF RHS 155A.

*Bract color, lower side.*—RHS 45C.

*Vein color, upper surface.*—RHS 45B.

*Vein color, lower surface.*—Approximately RHS 45B.

*Venation pattern.*—Pinnate.

*Texture.*—Weakly rugose, glabrous.

*Bract petiole color, upper surface.*—RHS 187B.

*Bract petiole color, lower surface.*—RHS 187C.

*Bract petiole, length.*—About 5.5 cm, shorter with younger bracts.

*Bract petiole diameter.*—0.2-0.3 cm.

Cyme (true inflorescence):

*Cyme, diameter.*—1.7-2.0 cm.

*Number of cyathia.*—5, borne in a tight cluster.

*Cyathium, shape.*—Ovate.

*Cyathium, diameter.*—0.2-0.5 cm.

*Cyathium, length.*—0.5-0.7 cm.

*Cyathium, texture.*—Smooth.

*Color.*—RHS 144A with RHS 146A spots, top is RHS 53B-C.

*Nectar cups.*—Usually one per cyathium.

*Nectar cup, width.*—0.3 cm.
*Nectar cup, length.*—0.5 cm.
*Nectar cup, color.*—RHS 144C.
*Nectar cup, shape.*—Oblong.
*Nectar cup, texture.*—Smooth.

Reproductive organs:

*Stamen* (*actually reduced male florets*).—Usually in a small bunch of 5-10 at the top of the cyathium.
*Shape.*—Strap-like.
*Filament length.*—0.2 cm.
*Filament color.*—RHS 53B to RHS 53C.
*Anther color.*—RHS 46A.
*Anther diameter.*—0.1 cm.
*Pollen quantity.*—Moderate (normal quantity).
*Pollen color.*—RHS 12A.
*Female flowers.*—Not yet observed.
*Fertility/seed set.*—Has not been observed on this plant.

Disease/pest resistance: Disease/pest resistance has not been observed on this plant.

What is claimed is:

1. A new and distinct variety of Poinsettia plant named 'EURZ0019', substantially as illustrated and described herein.

* * * * *